United States Patent [19]

Sudnak

[11] Patent Number: 4,894,055
[45] Date of Patent: Jan. 16, 1990

[54] NEEDLE GUARD ASSEMBLY FOR USE WITH HYPODERMIC SYRINGES AND THE LIKE

[76] Inventor: Paul J. Sudnak, 1210 Cote Sans Dessein, Fulton, Mo. 65251

[21] Appl. No.: 291,062

[22] Filed: Dec. 28, 1988

[51] Int. Cl.$^4$ .............................................. A61M 5/00
[52] U.S. Cl. ................................... 604/198; 604/263; 604/110
[58] Field of Search ............... 604/198, 263, 187, 136, 604/110

[56] References Cited

U.S. PATENT DOCUMENTS

| | | | |
|---|---|---|---|
| 4,737,144 | 4/1988 | Choksi | 604/198 |
| 4,747,831 | 5/1988 | Kulli | 604/198 X |
| 4,795,432 | 1/1989 | Karczmer | 604/198 |
| 4,813,940 | 3/1989 | Parry | 604/198 |

Primary Examiner—John D. Yasko
Attorney, Agent, or Firm—Haverstock, Garrett & Roberts

[57] ABSTRACT

A needle guard assembly for use in conjunction with a syringe or like device having a needle projecting from one end thereof comprising a first tubular member having one end constructed to cooperatively receive the needle end portion of a syringe with the needle extending therethrough, a second tubular member telescopingly positioned within the first tubular member and extending endwardly from the free end thereof, the second tubular member being movable between an extended position completely enclosing the needle and a retracted position, a spring member biasing the second tubular member to its extended position, bendable tab members located adjacent the free end of the first tubular member, and an annular member biasing the tab members outwardly so that the inner surface thereof is substantially coplanar with the inner surface of the first tubular member, movement of the second tubular member into the first tubular member moving the annular member out of engagement with the tab members thereby enabling the tab members to move inwardly behind the end edge of the second tubular member to restrict further movement thereof into the first tubular member when the spring member moves the second tubular member to its extended position. Other embodiments of the present device include various configurations associated with the locking mechanism and the positioning of the tab members associated therewith.

27 Claims, 4 Drawing Sheets

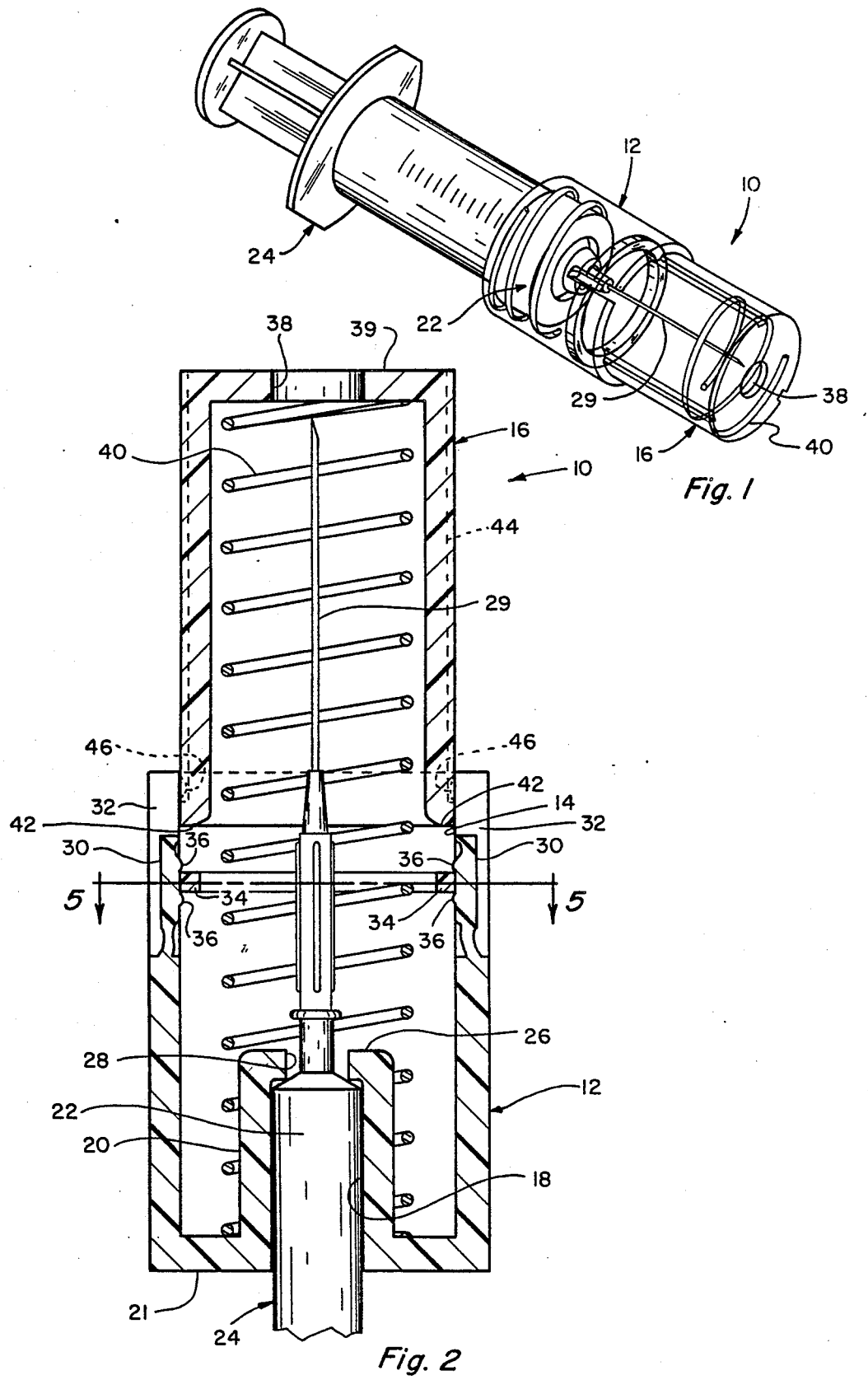

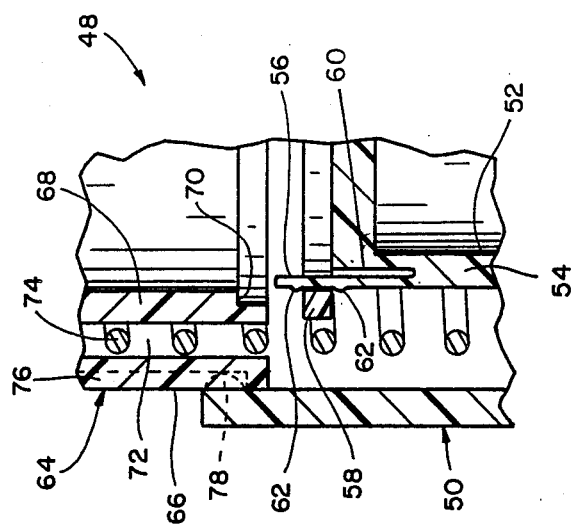
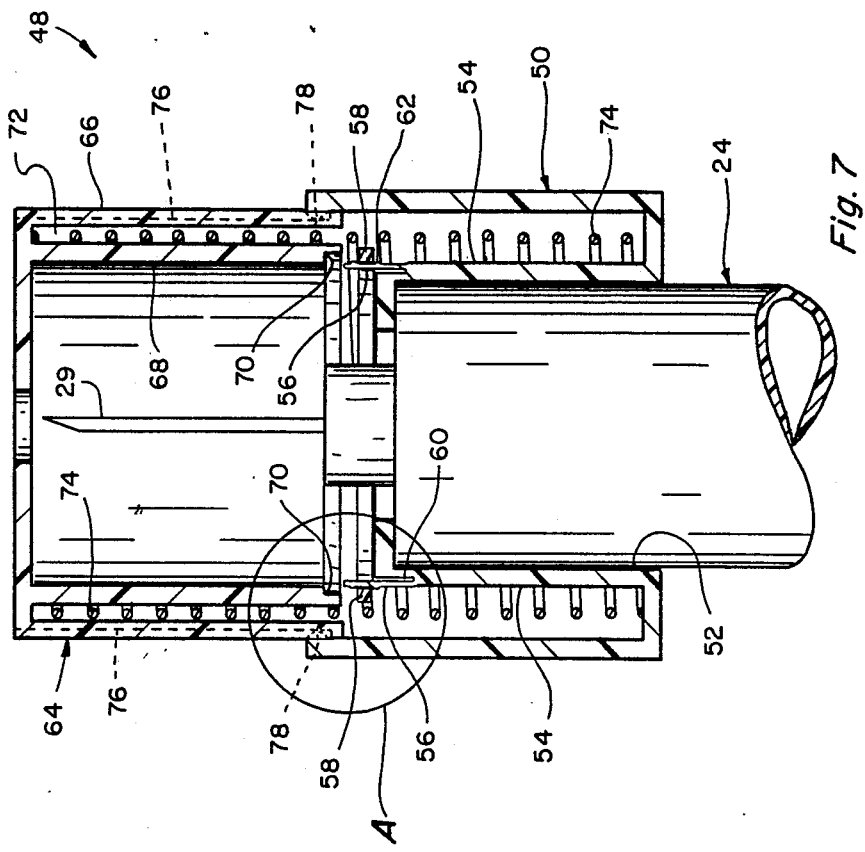

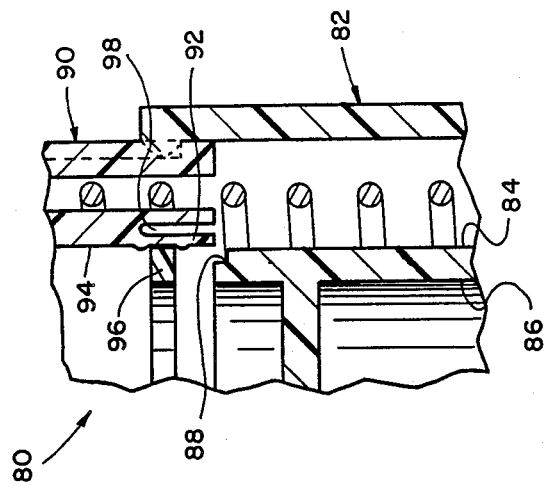
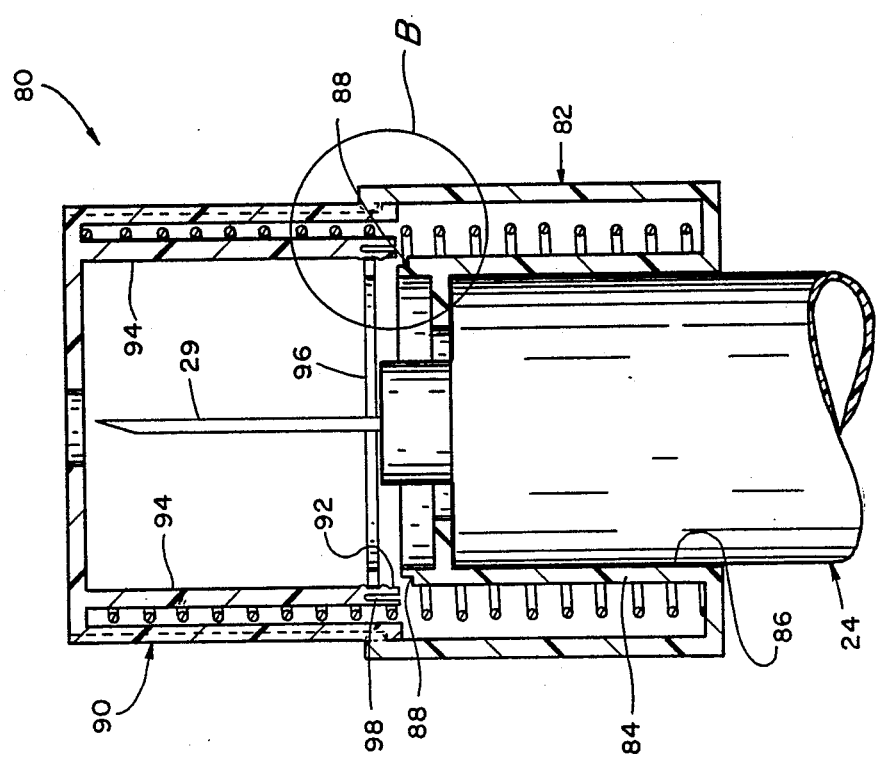

NEEDLE GUARD ASSEMBLY FOR USE WITH HYPODERMIC SYRINGES AND THE LIKE

BACKGROUND OF THE INVENTION

The present invention relates to a safety device for use in conjunction with hypodermic syringes and other similar needle-bearing medical appliances for protecting the users thereof from inadvertent punctures from contaminated needles. More particularly, the present invention relates to several embodiments of an improved needle guard assembly having a slidably movable guard member associated therewith, the guard member being movable between a retracted position wherein the syringe needle is fully exposed during use and an extended position wherein such needle is completely enclosed and encased within the guard member thereby safely housing the contaminated needle therewithin after use. The present assemblies also include a locking mechanism which automatically locks the protective guard member in its fully extended position around the contaminated needle after use thereby preventing further subsequent use of the devices. Although it is anticipated that the various embodiments of the present invention will be used primarily on hypodermic syringes, the present devices are likewise adaptable for use on a wide variety of other needle-bearing medical devices such as I.V. catheter placement units, blood-collecting apparatus and the like.

Contaminated hypodermic needles present a substantial health hazard and can result in transmission of a number of potentially life-threatening diseases such as hepatitis, acquired immune deficiency syndrome (AIDS), gonorrhea and other various diseases. One group which is particularly at risk in dealing with such devices are professional health care workers and housekeeping and janitorial personnel who must handle these skin-puncturing contaminated devices after they have been used. There, therefore, exists a great need to protect such personnel from accidental skin puncture injuries from such contaminated needles as well as a need to provide a safe and efficient means for disposing the same.

In an effort to provide some protection to health care workers and others, a wide variety of devices for shielding and guarding needles after use have been designed and manufactured. Such known devices teach a wide variety of constructions for accomplishing this task. For example, some of the known prior art constructions utilize complicated extension and retraction means for controlling the positioning of the shield or guard member about the used needle as well as complicated locking mechanisms for holding the shield member in place after use. See, for typical examples, the constructions shown in U.S. Pat. Nos. 4,664,654 and 4,752,290. Other known constructions are designed such that the entire exterior portion of the syringe becomes masked by the guard or shielding member when the device is retracted to expose the needle. See, for typical examples, the constructions shown in U.S. Pat. Nos. 4,738,663, 4,391,272 and 4,702,738. Still other examples of needle shielding devices are those shown and described in U.S. Pat. Nos. 3,890,971, 4,737,144 and 4,631,057. All such prior art devices suffer from certain disadvantages and shortcomings including being overly complex, expensive and difficult to manufacture, cumbersome to handle and install, hard to manipulate during operation, and many of such devices require manual retraction and/or extension of the guard or shield member before and after use. For these reasons, many of the prior art devices have proven to be ineffective and commercially unacceptable. In addition, none of the known needle shielding devices are as simple structurally as the present construction and none utilize as efficient and effective means for both retracting and extending the guard member during use and automatically locking the guard member in its fully extended position around the contaminated needle after use. For these and other reasons, most known needle shielding devices have enjoyed limited usefulness.

SUMMARY OF THE INVENTION

The present needle guard assembly overcomes many of the limitations and shortcomings associated with known needle shielding devices and teaches the construction and operation of a relatively simple needle guard device which effectively protects health care workers and others from accidental injuries by contaminated needle pricks. The present assembly includes a base member, a telescoping slidably movable guard member, spring means for normally biasing the guard member to its fully extended position completely surrounding the needle, and a novel locking mechanism for preventing subsequent use of the device as will be hereinafter explained. The base member is generally tubular in shape having one end portion open so as to telescopingly receive the guard member which is positioned therewithin. The opposite end portion of the base member includes a syringe port formed by flanged wall means, the syringe port being sized and dimensioned so as to snugly fit onto the barrel portion of a conventional syringe. The syringe port remains engaged with the syringe by means of friction, although adhesive means may likewise be applied to the interior wall surfaces of the syringe port to provide additional strength and stability to the joinder. Also, the syringe port can be fashioned and dimensioned to accommodate all known syringe sizes as well as other needle-bearing devices.

The present locking mechanism includes at least one pair of inwardly biased latching or tab members circumferentially spaced at an intermediate location on the base member. The resilient tab members are located in recesses formed in the interior wall portion of the base member near the one end portion thereof opposite the syringe port and such members are biased so as to extend into the interior area of the base member. An annular slip ring member is utilized to hold each respective tab member within its respective recess in flush alignment with the inner wall surface of the base member, the slip ring member being dimensioned so as to slide along the interior wall surface of the base member. The slip ring member prevents the resilient tab members from moving inwardly towards the interior portion of the base member into a position to engage the guard member and lock such member in its extended position as will be hereinafter explained. In order to help maintain the annular ring member in engagement with the respective latch or tab members prior to use of the present device, means in the form of small ridges or projections may be formed on the surface of the resilient tab members so as to capture and hold the slip ring member therebetween.

The present guard member is likewise tubular in shape and is slightly smaller in diameter as compared to the base member so as to be telescopingly engageable therewith. The guard member includes a reduced opening at one end portion thereof positioned so as to allow the needle associated with a hypodermic syringe or other needle-bearing device to extend therethrough when the guard member is retracted. The opposite end portion of the guard member is open and is telescopingly received in the open end portion of the base member. The guard member is slidably movable within the base member and, when the present device is engaged with a needle-bearing device, the guard member is movable between a retracted position wherein the needle is fully exposed during use and a fully extended position wherein the needle is completely enclosed within the guard member after use. Spring means positioned and located within the base and guard members bias the guard member to its fully extended position. Retraction of the guard member works against the biasing force exerted by the spring means.

The guard member may likewise include a plurality of spaced linear channels formed on the exterior surface thereof extending longitudinally therealong, the channels being positioned so as to register with a like plurality of circumferentially spaced inwardly extending projections formed on the interior wall surface of the base member near the one end portion thereof opposite the syringe port. Registration of the guard channels with the base projections prevents the guard member from being totally withdrawn from within the base member as the terminal end portion of each of the respective channels serves as a stop means when the respective projections are engaged therewith. Also, this arrangement prevents any rotational movement of the guard member within the base member. It is recognized that a wide variety of stop means may be utilized with the present assembly for preventing the guard member from being totally withdrawn from within the base member.

To operate the present device, the annular slip ring member is first positioned within the base member in engagement with the latch or tab members so that the tab members are held within their respective recesses in flush alignment with the inner wall surface of the base member. The guard member is then telescopingly positioned within the base member so as to engage the spring means. The present device is then attached to the hypodermic syringe or other needle-bearing medical device by inserting the same within the syringe port of the base member. At this point, the syringe needle in fully enclosed and encased by the guard member. Also, the biasing action of the spring means prevents the terminal end portion of the guard member positioned within the base member from making contact with the slip ring member. The present device is now in its pre-injection position and is ready for use. Importantly, it is anticipated that the present device may be packaged in a pre-assembled condition so that a user need only attach the device to a syringe or other needle-bearing device prior to use.

Upon the giving of an injection, the sliding guard member retracts into the base member allowing the syringe needle to be fully exposed and inserted into the skin tissue of a patient. During this process, the locking mechanism is triggered meaning that the slip ring member is forced by the sliding guard member out of its original position in contact with the inwardly biased latch or tab members and towards the bottom portion of the base member. When the needle is withdrawn from the skin tissue of a patient, the tension of the spring means moves the guard member from its retracted position inside the base member towards its fully extended position completely shielding the syringe needle thereby enabling the then exposed, unrestrained latch or tab members to engage a locking seat located on the sliding guard member thus preventing the guard member from further retracting into the base member a second time. Following its one-time use, the entire device with the syringe needle fully enclosed therewithin can be disposed of.

Other embodiments of the present device include various configurations associated with the locking mechanism and the positioning of the latching members associated therewith. For example, one embodiment of the present device includes locating the resilient latching members on the guard member of the present assembly, while still another embodiment includes locating the latching members on the flanged wall means associated with the syringe port. Regardless of where the resilient latching members are positioned, the several embodiments of the present invention operate substantially similarly as will be hereinafter explained.

It is therefore a principle object of the present invention to provide safe and reliable means for protecting health care workers and others from accidentally sticking themselves with contaminated needles.

Another object is to provide a needle guard assembly which can be fabricated to easily attach to any conventional syringe or other needle-bearing device.

Another object is to provide an easy to use needle guard assembly which automatically encases the contaminated needle after use.

Another object is to provide a needle guard assembly which does not interfere with the operation of the syringe or other needle-bearing device.

Another object is to teach the construction of a needle guard assembly which utilizes at least one pair of spaced resilient tab members for maintaining the guard member in its fully extended position encasing the contaminated needle once the needle has been used.

Another object is to provide a fail-proof method of permanently securing contaminated needles.

Another object is to provide a needle guard assembly having means associated therewith for preventing a contaminated needle from being reused.

Another object is to provide a needle guard assembly that is structurally and operationally relatively simple and inexpensive to make.

Another object is to provide a needle guard assembly which is easy to install and use.

Another object is to provide a needle guard assembly which allows full visual exposure of the needle as well as observation for blood when the syringe is aspirated.

Another object is to teach the construction of a needle guard assembly which prevents damage to the needle both prior to and during use.

Another object is to teach the construction of a telescopic needle guard assembly which provides for the safe disposal of contaminated needles.

These and other objects and advantages of the present invention will become apparent to those skilled in the art after considering the following detailed specification which discloses several different embodiments of the present device in conjunction with the accompanying drawings.

BRIEF DESCRIPTION OF THE DRAWINGS

FIG. 1 is a perspective view of a needle guard assembly constructed according to the teachings of the present invention wherein only portions of the spring member are illustrated for clarity;

FIG. 2 is an enlarged fragmentary cross-sectional view showing the needle guard assembly of FIG. 1 in its extended pre-injection position;

FIG. 7 is an enlarged fragmentary cross-sectional view showing another embodiment of the present needle guard assembly in its extended pre-injection position;

FIG. 7A is an enlarged fragmentary cross-sectional view of region A of FIG. 7 showing one of the latching members in engagement with the slip ring member;

FIG. 8 is an enlarged fragmentary cross-sectional view showing still another embodiment of the present needle guard assembly in its extended pre-injection position; and FIG. 8A is an enlarged fragmentary cross-sectional view of region B of FIG. 8 showing one of the latching members in engagement with the slip ring member.

DESCRIPTION OF THE PREFERRED EMBODIMENT

Figure 3:
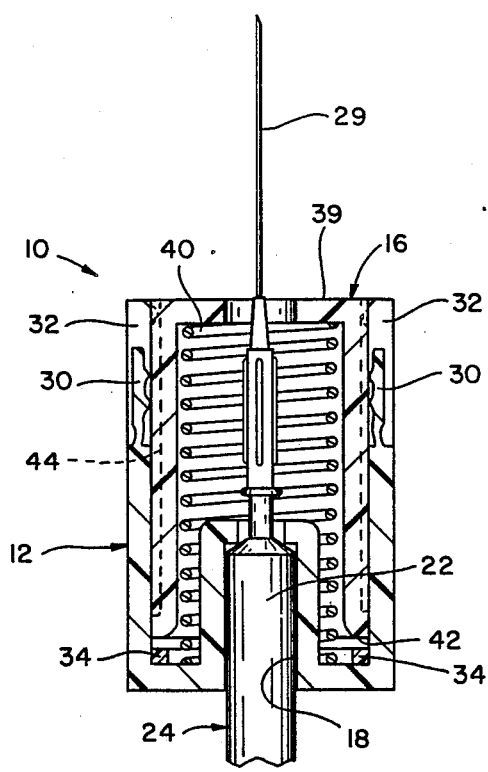
FIG. 3 is a fragmentary cross-sectional view showing the present needle guard assembly in its retracted position.

Referring to the drawings more particularly by reference numbers wherein like numerals refer to like parts, number 10 in FIGS. 1 and 2 identifies a preferred embodiment of a needle guard assembly constructed according to the teachings of the present invention. Referring more particularly to FIG. 2, the needle guard assembly 10 includes an elongated substantially tubular base member 12 having an opening 14 associated with its upper end portion adaptable for telescopingly receiving the guard member 16 which is positioned therewithin. The opposite end portion of the base member 12 includes a syringe port 18 formed by the annular wall means 20, the syringe port 18 being dimensioned to frictionally or otherwise engage the barrel portion 22 associated with a conventional syringe such as the syringe 24. The syringe port 18 is partially closed at its upper end by the flange portion 26 thereby forming a reduced opening 28 of sufficient size to enable the needle portion 29 of the syringe 24 to extend therethrough as best shown in FIG. 2. The flange 26 forms a stop means for the syringe barrel 22 and prevents longitudinal movement of the syringe within the port 18 during the giving of an injection. Although the frictional engagement between the port 18 and the syringe barrel 22 is sufficient to maintain the present device in stable engagement with the syringe during use thereof, adhesive means (not shown) may likewise be applied to the interior wall surfaces of the syringe port 18 to provide additional strength and stability thereto. Also, importantly, the syringe port 18 can be fashioned and dimensioned so as to accommodate all known syringe sizes.

Figure 5:
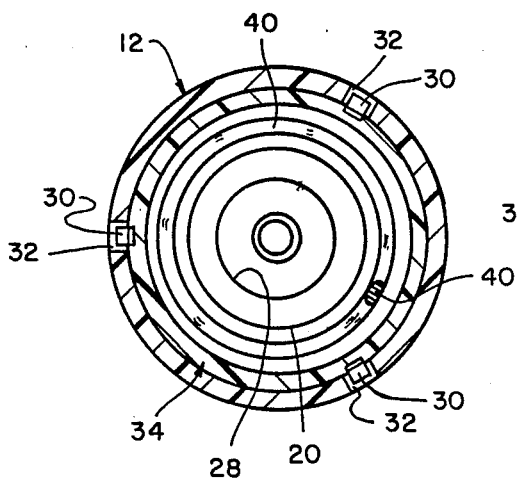
FIG. 5 is a cross-sectional view taken along line 5—5 of FIG. 2.

The upper end portion of the base member 12 includes at least one pair of inwardly biased tab or latching members 30 circumferentially spaced at an intermediate location along the interior wall surface of the member 12 as shown in FIGS. 2 and 5. The resilient tab members 30 are located in respective recesses 32 formed in the interior wall of the member 12 near the upper end portion thereof and are preferably integrally formed with such wall means as shown. Importantly, the members 30 are sufficiently biased so as to extend into the interior area of the base member 12 when left unrestrained. In this regard, an annular slip ring member 34 is positioned within the opening 14 and is utilized to hold each respective tab member 30 in its respective recess 32 in flush alignment with the inner wall surface of the base member 12 as shown in FIG. 2. The ring member 34 is dimensioned so as to frictionally engage the interior wall surface of the base member 12 when positioned therewithin and it can be slid along such wall surface until it is positioned in engagement with the respective tab members 30. The annular member 34 remains engaged with the tab members 30 by means of friction as well as by the inward bias associated with each respective tab member 30.

Optional means in the form of small ridges or projections such as the projections 36 can be formed on the surface of the members 30 as best shown in FIG. 2, the projections 36 being spaced so as to capture and hold the annular ring member 34 therebetween. It is also anticipated that a wide variety of other means such as longitudinally extending ridge means (not shown) may likewise be formed on the surface of the respective tab members 30 to help maintain the annular member 34 in positive engagement with the tab members 30, such other means further increasing the frictional engagement between the members 30 and 34. Any plurality of resilient tab members 30 may be utilized with any particular assembly 10 depending upon the overall size of the particular device as well as the specific application for which it is designed.

The elongated guard member 16 is likewise substantially tubular in shape and is dimensioned so as to be telescopingly receivable within the opening 14 of the base member 12. The guard member 16 includes a reduced opening 38 at its upper end portion, the opening 38 being positioned so as to allow the needle 29 to extend therethrough when the member 16 is retracted as will be hereinafter explained. The opposite end portion of the member 16 is open and is telescopingly engageable with the base member 12 as previously explained. The member 16 is slidably movable within the member 12 between a fully extended position shown in FIG. 2 wherein the needle 29 is completely enclosed and encased within the guard member 16 and a retracted position as shown in FIG. 3 wherein the needle 29 is fully exposed such as during the giving of an injection to a patient when the needle is fully inserted within the patient's body tissue.

Figure 4:
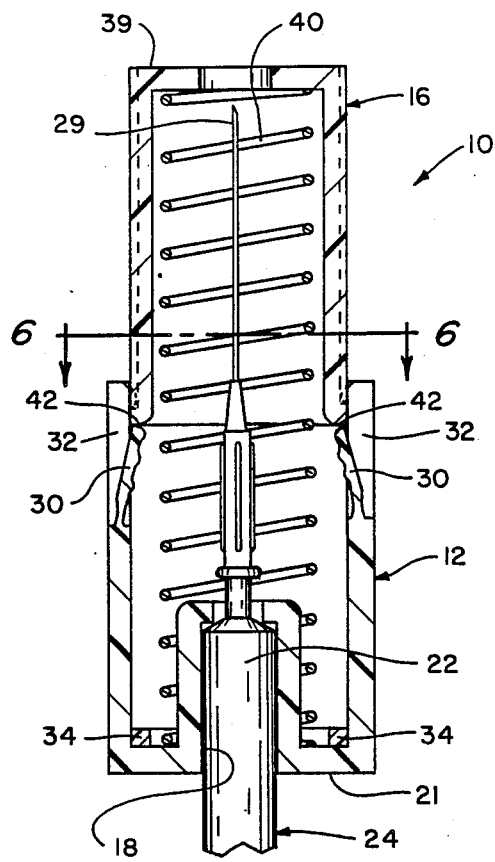
FIG. 4 is a fragmentary cross-sectional view showing the present needle guard assembly in its extended post-injection position.

Biasing means in the form of the spring member 40 is positioned and located within the respective members 12 and 16 such that the guard member 16 is always biased to its fully extended position as shown in FIGS. 2 and 4. One end portion of the spring 40 engages the bottom wall means 21 of the member 12 while its opposite end portion engages the upper wall means 39 of the member 16. When so positioned, the spring 40 exerts a constant force on the respective walls 21 and 39 thereby constantly urging the guard member 16 towards its fully extended position. The spring member 40 is also preferably dimensioned so as to frictionally engage the syringe port 18. This serves as an anchoring means and enables the spring 40 to remain relatively secure within the assembly 10. Also, importantly, the overall length of the spring member 40 must be such that when the guard member 16 is biased to its fully extended position as shown in FIG. 2, the terminal end portion 42 of the member 16 is spaced from and does not make contact with the annular ring member 34. This is important so that the resilient tab members 30 are not triggered to their locking positions as will be hereinafter explained.

Figure 6:
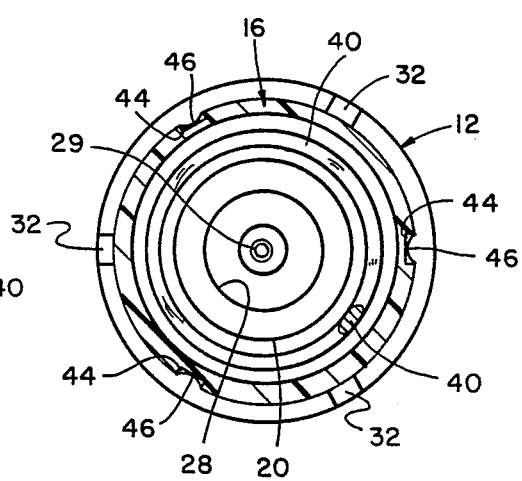
FIG. 6 is a cross-sectional view taken along line 6—6 of FIG. 4.

The guard member 16 may likewise include a plurality of spaced linear channels 44 formed on the exterior surface of the member 16 extending longitudinally therealong as best shown in FIG. 2. The respective channels 44 are positioned so as to register with a like plurality of circumferentially spaced inwardly extending projections 46 formed on the interior wall surface of the base member 12 near the upper end portion thereof as shown in FIGS. 2 and 6. The longitudinal channels 44 extend substantially the entire length of the member 16 and terminate just above the terminal end portion 42 as shown in FIG. 2. When the projections 46 are engaged with the channels 44, rotational movement of the guard member 16 within the base member 12 is prohibited. Also, this arrangement prevents the guard member 16 from being totally withdrawn from the base member 12 as the terminal end portion of each of the respective channels 44 serves as a stop means when the respective projections 46 are engaged therewith. Like the resilient tab members 30, any number of corresponding channels 44 and projections 46 may be utilized with any particular embodiment 10 depending upon the overall size of the assembly 10 as well as the particular application for which it is designed.

FIG. 2 illustrates the present needle guard assembly 10 in its extended pre-injection position. As previously explained, this position is achieved by first engaging the annular ring member 34 with the resilient tab members 30 so that such members are held in flush alignment with the inner wall surface of the base member 12. The guard member 16 is then telescopingly positioned within the base member 12 so as to engage the spring means 40. The present device 10 is then attached to the hypodermic syringe 24 or other needle-bearing device by inserting the same within the syringe port 18 as previously explained. The present device 10 is now ready for use as illustrated in FIG. 2. It is also anticipated that the present device 10 may be packaged in a pre-assembled condition so that it may be quickly attached to a needle-bearing device or, still further, the device 10 may be packaged so that it is already attached to a needle-bearing device and is ready for immediate use.

In the case of giving an injection, the upper wall means 39 is positioned adjacent the patient's skin tissue at the injection site and the needle 29 is advanced so as to penetrate the skin. The force exerted in advancing the needle 29 will cause the guard member 16 to automatically retract within the base member 12. As the guard member 16 moves towards the syringe port 18, the terminal end portion 42 of the member 16 engages the annular ring member 34 and forces the member 34 out of frictional engagement with the resilient tab members 30 and towards the bottom portion of the member 12. Once the needle 29 is fully inserted within the patient's skin tissue, the guard member 16 will have achieved its fully retracted position as shown in FIG. 3.

In this position, the inwardly biased resilient tab members 30 are now held in flush alignment with the inner wall surface of the base member 12 by the exterior wall surface of the guard member 16. When the needle 29 is withdrawn from the patient, the tension of the spring member 40 exerts a force on the upper wall means 39 so as to automatically move the guard member 16 from its retracted position inside the base member 12 (FIG. 3) towards its fully extended position completely shielding the syringe needle 29 as shown in FIG. 4. As the terminal end portion 42 of the member 16 passes the respective tab members 30, the tab members 30 are urged away from the recesses 32 and extend inwardly towards the interior portion of the member 12 so as to subsequently engage the end portion 42 as best shown in FIG. 4. This forms a locking seat due to the blockage created by the extended tab members 30 thus preventing any further use of the device 10. A user can now easily and safely discard the entire device 10 including the syringe 24 attached thereto.

All of the features and capabilities afforded by the present device 10 including, in particular, its ability to automatically retract and extend the guard member 16 during use and its ability to automatically lock the guard member 16 in its fully extended position around the contaminated needle after a one-time use thereof, represent important advancements in this particular art.

FIGS. 7 and 7A disclose another embodiment 48 of a needle guard assembly constructed according to the teachings of the present invention. The assembly 48 includes a substantially tubular base member 50 having a syringe port 52 associated therewith as shown in FIG. 7. The syringe port 52 extends upwardly into the interior area of the base member 50 a much greater distance as compared to the port 18 associated with the assembly 10 (FIGS. 2-4). This is necessary because each of the respective resilient tab members 56 is now positioned and located adjacent the upper portion of the annular wall means 54 forming the syringe port 52. Like the tab members 30 (FIGS. 2-4), each tab member 56 is normally biased so as to extend into the interior area of the base member 50. An annular ring member 58 substantially similar to the member 34 (FIGS. 2-4) is likewise utilized to hold each respective tab member 56 in its respective cavity or space 60 in flush alignment with the outer wall surface of the wall means 54. As with the resilient tab members 30, it is preferred that the tab members 56 likewise be integrally formed with the wall means 54 as shown in FIG. 7A. Also, the tab members 56 may likewise include means in the form of small ridges or projections such as the projections 62 so as to help maintain the annular ring member 58 in tight frictional engagement with the respective tab members 56 as previously explained.

The guard member 64 is also substantially tubular in shape and is dimensioned so as to be telescopingly received within the base member 50 as shown in FIG. 7. The guard member 64 differs from the guard member 16 in that it includes a double wall construction defined by outer wall means 66 and inner wall means 68. The interior wall means 68 extends downwardly the full length of the member 64 and includes a notch or cutout 70 at the terminal end portion thereof which forms a locking seat for engaging the resilient tab members 56 as will be hereinafter explained. An annular space 72 is formed between the respective wall means 66 and 68, the space 72 being dimensioned so as to receive the spring member 74 as shown in FIG. 7. The space 72 serves as an anchoring means for the spring member 74 and enables the spring 74 to remain relatively secure within the assembly 48. It is important that the annular ring member 58 hold each respective tab member 56 in flush alignment with the wall means 54 so that the interior wall 68 of the member 64 does not engage or otherwise interfere with the respective tab members as the guard member 64 is moved to its fully retracted position.

Operation of the assembly 48 is somewhat similar to the operation of the assembly 10 in that as the guard member 64 is retracted within the base member 50, the terminal end portion of the inner wall member 68 engages the annular ring member 58 and forces such member out of frictional engagement with the resilient tab members 56 and towards the bottom portion of the base member 50. When the guard member 64 is fully retracted within the member 50, the annular ring member 58 is forced to the bottom of the member 50 and the outwardly biased resilient tab members 56 are now held in flush alignment with the outer wall surface of the wall means 54 by the wall means 68. In this regard, it is important to note that the annular ring member 58 travels between the wall means 54 and the spring member 74. It is therefore important that sufficient space be provided therebetween so that the member 58 does not interfere with the operation of the spring 74 and does not bind or otherwise jam so as to prevent retraction of the guard member 64. Upon extension of the guard member 64, as the terminal end portion of the wall means 68 passes the respective tab members 56, the tab members 56 move out of the spaces 60 and extend outwardly towards the interior portion of the base member 50 so as to subsequently engage the locking seat 70. This prevents the guard member 64 from further retracting into the base member 50.

Similar to the embodiment 10 illustrated in FIGS. 2-4, the assembly 48 may likewise include a plurality of spaced linear channels 76 formed and positioned on the exterior surface of the wall means 66 so as to register with a like plurality of circumferentially spaced inwardly extending projections 78 formed on the upper end portion of the base member 50. As previously explained, this arrangement prevents relative rotational movement between the members 50 and 64 and it further prevents the guard member 64 from being totally withdrawn from the base member 50. Also, importantly, the length of the wall means 54 forming the syringe port 52 is predicated upon the length of the needle 29 and the amount of retraction necessary by the member 64 in order to achieve a fully exposed needle. This will also affect the overall length of the base member 50 as well.

FIGS. 8 and 8A illustrate still another embodiment 80 of the present needle guard assembly. The assembly 80 includes a base member 82 which is substantially similar in construction to the base member 50 but differs therefrom in that the annular wall means 84 forming the syringe port 86 includes a notch or cutout 88 located at the upper end portion thereof. The guard member 90 is substantially similar in construction to the member 64 but differs therefrom in that the resilient tab members 92 are positioned and located adjacent the terminal end portion of the interior wall means 94. An annular ring member 96 is positioned within the guard member 90 and is utilized to hold each respective tab member 92 in its respective cavity or space 98 in flush alignment with the inner wall surface of the wall means 94 as shown in FIGS. 8 and 8A. As the guard member 90 is retracted within the base member 82, the annular wall means 84 engages the ring member 96 thereby forcing the member 96 out of engagement with the resilient tab members 92 and towards the upper portion of the guard member 90. When fully retracted, the resilient tab members 92 are held in flush alignment with the inner wall surface of the wall means 94 within the spaces 98 by the wall means 84. Upon extension of the guard member 90, as the resilient tab members 92 move pass the terminal end portion of the wall means 84, the tab members 92 extend inwardly towards the interior portion of the member 90 and subsequently engage the locking seat 88 thereby preventing any further use of the device 80. In all other respects, the base member 82 and the guard member 90 are constructed and arranged similarly to the members 12, 16, 50 and 64 as previously described.

Although it is recognized that various acceptable materials of construction are available and could equally be employed to fabricate the various components associated with the several embodiments of the present needle guard assembly disclosed herein, it is usually preferred that the present devices be made of a transparent material such as a clear strong plastic material so that health care workers are able to see through the devices while giving an injection or otherwise using the needle-bearing appliance. This is particularly advantageous because it provides a user with a clear view of the needle at all times; it allows for clear observation of the injection site; it allows for clear observation of the medication within the particular syringe; and it enables a user to observe for blood when a syringe is aspirated prior to use. Also, regardless of the type of materials employed, the present devices protect the enclosed needle by shielding the same both prior to and during use thereby substantially eliminating damage thereto; they provide a more sterile field than a capped needle up to the point of insertion; and they provide a more sterile atmosphere in and around the injection site by keeping debris and other foreign substances away from the injection area.

Thus, there has been shown and described several embodiments of a novel needle guard assembly for protecting health care workers and others from accidental skin punctures from contaminated needles, which assemblies fulfill all of the objects and advantages sought therefor. Many changes, modifications, variations, and other uses and applications of the present constructions will, however, become apparent to those skilled in the art after considering this specification and the accompanying drawings. All such changes, modifications, variations, and other uses and applications which do not depart from the spirit and scope of the invention are deemed to be covered by the invention which is limited only by the claims which follow.

What is claimed is:

1. A needle guard assembly for use in conjunction with a syringe device having a needle projecting from one end portion thereof comprising a first tubular member having spaced opposed end portions and an inner and outer surface, said first tubular member having means associated with one end portion thereof for cooperatively receiving the needle end portion of a syringe device with the needle extending therethrough, a second tubular member telescopingly positioned within said first tubular member and extending endwardly from the free end portion of said first tubular member, said second tubular member being movable between an extended position and a position wherein said member is at least partially retracted within said first tubular member, means biasing said second tubular member to its extended position, bendable tab means associated with said first tubular member adjacent the free end portion thereof including means biasing said tab means outwardly so that the inner surface thereof is substantially coplanar with the inner surface of said first tubular member, movement of said second tubular member into said first member moving the means biasing said tab means out of engagement with said tab means enabling said tab means to move inwardly behind the one end portion of said second tubular member when said biasing means moves said second tubular member to its extended position thereby preventing said second tubular member from again moving into said first tubular member.

2. The needle guard assembly defined in claim 1 wherein said means biasing said tab means includes an annular member positioned within said first tubular member.

3. The needle guard assembly defined in claim 1 including a plurality of bendable tab means associated with said first tubular member.

4. The needle guard assembly defined in claim 1 including cooperatively engageable means associated with said first and second tubular members for preventing said second tubular member from moving out of said first tubular member.

5. The needle guard assembly defined in claim 1 including means to prevent relative rotational movement between said first and second tubular members.

6. The needle guard assembly defined in claim 1 wherein said tab means includes at least one protuberance formed on the inner surface thereof.

7. The needle guard assembly defined in claim 4 wherein said cooperatively engageable means for preventing said second tubular member from moving out of said first tubular member includes at least one projection located on the inner surface of said first tubular member adjacent the free end portion thereof, and means located on the outer surface of said second tubular member adjacent one end portion thereof for engaging the projection on said first tubular member when said second tubular member is in its extended position.

8. The needle guard assembly defined in claim 5 wherein said means to prevent relative rotational movement between said first and second tubular members includes at least one projection located on the inner surface of said first tubular member, and at least one correspondingly shaped channel extending longitudinally along the outer surface of said second tubular member, said projection being cooperatively engageable with said channel when said second tubular member is telescopingly positioned within said first tubular member.

9. Means for protectively shielding the needle associated with a needle-bearing device comprising a tubular base member having opposed end portions and an inner and outer surface, said tubular base member having one end portion thereof formed to cooperatively receive the needle portion of a needle-bearing device such that the free end portion thereof circumscribes a portion of the length of the needle extending therethrough, a tubular guard member slidably movable within said base member between an extended and a retracted position, said guard member circumscribing the needle over the rest of the length thereof when in its extended position and having end wall means partially closing the free end portion thereof, spring means biasing said guard member into its extended position, bendable tab means on said base member adjacent the free end portion thereof for holding said guard member in its extended position when advanced thereto from its retracted position, means biasing said tab means outwardly so that the inner surface thereof is substantially flush with the inner surface of said base member, movement of said guard member into said base member towards its retracted position moving the means biasing said tab means out of engagement with said tab means thereby enabling said tab means to move inwardly behind the one end portion of said guard member when said guard member is moved from its retracted position to its extended position.

10. The means defined in claim 9 wherein said base and guard members are made of a transparent material.

11. The means defined in claim 9 including a plurality of bendable tab means circumferentially spaced on said base member adjacent the free end portion thereof.

12. The means defined in claim 11 wherein said means biasing said tab means includes an annular member, said annular member biasing each of said plurality of tab means outwardly so that the inner surface of each respective tab means is substantially flush with the inner surface of said base member.

13. Means to prevent reuse of a syringe device having a needle projecting from one end portion thereof, said means including a first tubular member having spaced opposed end portions and an inner and outer surface, one end portion of said first tubular member including means for cooperatively receiving and engaging the needle portion of a syringe device with the needle extending therethrough, the free end portion of said first tubular member circumscribing a portion of the length of the needle, a second tubular member positioned to be telescopingly slidable in said first tubular member and extending endwardly from said first tubular member to circumscribe the needle over the rest of the length thereof, spring means biasing said second tubular member outwardly from said first tubular member, bendable tab means on said first tubular member adjacent the free end thereof including means biasing the tab means outwardly so that the inner surface thereof is substantially coplanar with the inner surface of said first tubular member, movement of said second tubular member into said first tubular member during the giving of an injection moving the means biasing said tab means out of engagement with said tab means whereby said tab means are able to move inwardly behind the one end portion of said second tubular member when said spring means moves said second tubular member to an extended position after the giving of an injection to prevent said second tubular member from again moving into said first tubular member.

14. A needle guard assembly for use in conjunction with a syringe device having a needle projecting from one end portion thereof comprising a first tubular member having spaced opposed end portions and an inner and outer surface, wall means extending into said first tubular member from adjacent one end portion thereof forming a port for cooperatively receiving the needle end portion of a syringe device with the needle extending therethrough, a second tubular member telescopingly positioned within said first tubular member and extending endwardly from the free end portion thereof so as to circumscribe the needle over the remainder of the length thereof, said second tubular member having spaced parallel inner and outer walls and being movable between an extended position and a position wherein said second tubular member is at least partially retracted within said first tubular member, means biasing said second tubular member to its extended position, bendable tab means located on the inner wall of said second tubular member adjacent the end portion thereof positioned within said first tubular member, means biasing said tab means outwardly so that the inner surface thereof is substantially coplanar with the inner surface of the inner wall of said second tubular member, movement of said second tubular member into said first tubular member moving the means biasing said tab means out of engagement with said tab means thereby enabling said tab means to move inwardly in front of said port wall means when said biasing means moves said second tubular member to its extended position, said tab means thereafter engaging said port wall means thereby preventing said second tubular member from ag in moving into said first tubular member.

15. The needle guard assembly defined in claim 14 wherein said means biasing said tab means includes an annular member positioned within said second tubular member.

16. The needle guard assembly defined in claim 14 wherein said port wall means extend to substantially adjacent the free end portion of said first tubular member.

17. The needle guard assembly defined in claim 14 wherein at least a portion of said means biasing said second tubular member to its extended position extends into the space formed by and between the inner and outer walls of said second tubular member.

18. The needle guard assembly defined in claim 14 including a plurality of bendable tab means circumferentially spaced on the inner wall of said second tubular member.

19. The needle guard assembly defined in claim 14 including cooperatively engageable means associated with said first and second tubular members for preventing said second tubular member from moving out of said first tubular member.

20. The needle guard assembly defined in claim 14 including means to prevent relative rotational movement between said first and second tubular members.

21. The needle guard assembly defined in claim 14 wherein said tab means includes at least one projection formed on the inner surface thereof.

22. A needle guard assembly for use in conjunction with a syringe device having a needle projecting from one end portion thereof comprising a first tubular member having spaced opposed end portions and an inner and outer surface, wall means extending into said first tubular member from adjacent one end portion thereof forming a port for cooperatively receiving the needle end portion of a syringe device with the needle extending therethrough, a second tubular member telescopingly positioned within said first tubular member and extending endwardly from the free end portion thereof so as to circumscribe the needle over the remainder of the length thereof, said second tubular member having spaced parallel inner and outer walls and being movable between an extended position and a position wherein said second tubular member is at least partially retracted within said first tubular member, means biasing said second tubular member to its extended position, bendable tab means located on said port wall means including means biasing said tab means inwardly so that the outer surface thereof is substantially coplanar with the outer surface of said port wall means, movement of said second tubular member into said first tubular member moving the means biasing said tab means out of engagement with said tab means enabling said tab means to move outwardly behind the one end portion of the inner wall of said second tubular member when said biasing means moves said second tubular member to its extended position thereby preventing said second tubular member from again moving into said first tubular member.

23. The needle guard assembly defined in claim 22 wherein said means biasing said tab means includes an annular member.

24. The needle guard assembly defined in claim 22 wherein at least a portion of said means biasing said second tubular member to its extended position extends into the space formed by and between the inner and outer walls of said second tubular member.

25. The needle guard assembly defined in claim 22 including a plurality of bendable tab means located on said port wall means.

26. The needle guard assembly defined in claim 22 including cooperatively engageable means associated with said first and second tubular members for preventing said second tubular member from moving out of said first tubular member.

27. Means to prevent re-insertion of a second tubular member into a first tubular member comprising a first tubular member having an inner cylindrical surface and spaced opposed end portions, end wall means at least partially closing one of the opposed end portions of said first tubular member, a second tubular member having an outer surface of substantially the same diameter as the inner surface of said first tubular member, said second tubular member being telescopingly positioned in said first tubular member and movable therein between an extended and a retracted position, said second tubular member having end wall means partially closing the free end portion thereof, means biasing said second tubular member into its extended position in said first tubular member, tab means on said first tubular member adjacent to the free end portion thereof having an inner surface and an end face, means in said first tubular member biasing said tab means outwardly so that the inner surface of said tab means is substantially coplanar with the inner surface of said first tubular member, said second tubular member moving the means biasing said tab means out of engagement with said tab means when said second tubular member is slidably moved into said first tubular member whereby when said second tubular member is again moved to its extended position out of said first tubular member the end face of said tab means is able to move behind the end edge of said second tubular member thereby preventing further movement of said second tubular member into its retracted position in said first tubular member.

* * * * *

UNITED STATES PATENT AND TRADEMARK OFFICE
CERTIFICATE OF CORRECTION

PATENT NO. : 4,894,055
DATED      : January 16, 1990
INVENTOR(S) : Paul J. Sudnak It is certified that error appears in the above-identified patent and that said Letters Patent is hereby corrected as shown below:

Column 13, line 19, "ag in" should be --again--.

Signed and Sealed this

Twenty-second Day of January, 1991

Attest:

HARRY F. MANBECK, JR.

*Attesting Officer*        *Commissioner of Patents and Trademarks*